United States Patent
Moore et al.

(10) Patent No.: US 7,298,816 B2
(45) Date of Patent: Nov. 20, 2007

(54) TOMOGRAPHY SYSTEM

(75) Inventors: Richard H. Moore, Concord, MA (US); Daniel B. Kopans, Waban, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/195,463

(22) Filed: Aug. 2, 2005

(65) Prior Publication Data

US 2007/0104314 A1    May 10, 2007

(51) Int. Cl.
*A61B 6/04* (2006.01)
(52) U.S. Cl. .......................... 378/37; 378/197
(58) Field of Classification Search ............ 378/37, 378/21–27
See application file for complete search history.

(56) References Cited

U.S. PATENT DOCUMENTS

| | | |
|---|---|---|
| 3,746,872 A | 7/1973 | Ashe et al. |
| 4,442,534 A | 4/1984 | Haendle et al. |
| 4,922,512 A | 5/1990 | Lajus et al. |
| 5,060,246 A | 10/1991 | Van Der Brug et al. |
| 5,359,637 A | 10/1994 | Webber |
| 5,511,106 A | 4/1996 | Doebert et al. |
| 5,872,828 A | 2/1999 | Niklason et al. |
| 6,005,908 A | 12/1999 | Oppelt et al. |
| 6,164,820 A | 12/2000 | Hell et al. |
| 6,233,303 B1 | 5/2001 | Tam |
| 6,242,743 B1 | 6/2001 | DeVito et al. |
| 6,285,733 B1 | 9/2001 | Proksa et al. |
| 6,289,235 B1 | 9/2001 | Webber et al. |
| 6,292,531 B1 | 9/2001 | Hsieh |
| 6,341,156 B1 | 1/2002 | Baetz et al. |
| 6,375,352 B1 | 4/2002 | Hewes et al. |
| 6,545,280 B2 | 4/2003 | Weinberg |
| 6,574,499 B1 | 6/2003 | Dines et al. |
| 6,600,803 B2 | 7/2003 | Bruder et al. |
| 6,611,575 B1 | 8/2003 | Alyassin et al. |
| 6,618,466 B1 | 9/2003 | Ning |
| 6,765,981 B2 | 7/2004 | Heumann |
| 2002/0045833 A1 | 4/2002 | Wake et al. |
| 2002/0104163 A1 | 8/2002 | Reimann |
| 2002/0181649 A1 | 12/2002 | Rasche et al. |

(Continued)

FOREIGN PATENT DOCUMENTS

DE    0 224 886    6/1987

(Continued)

OTHER PUBLICATIONS

Budinger, "Biological and Biomedical Imaging;" Whitaker Summit White Paper: Biological and Biomedical Imaging; Biomedical Engineering Educational Summit Meeting 2000; 4 pages.

(Continued)

*Primary Examiner*—Hoon Song
(74) *Attorney, Agent, or Firm*—Daly, Crowley, Mofford & Durkee, LLP (57) ABSTRACT

A measurement system is presented. The measurement system includes a source and a detector located a selected distance from the source with the source and the detector movable about a point, an axis or about a plane located proximate the detector.

19 Claims, 4 Drawing Sheets

U.S. PATENT DOCUMENTS

| | | |
|---|---|---|
| 2003/0043962 A1 | 3/2003 | Lai |
| 2003/0194050 A1 | 10/2003 | Eberhard et al. |
| 2003/0194051 A1 | 10/2003 | Wang et al. |
| 2004/0131145 A1* | 7/2004 | Ohara .......................... 378/37 |
| 2005/0089123 A1 | 4/2005 | Bruder et al. |
| 2005/0113681 A1* | 5/2005 | DeFreitas et al. ........... 600/426 |
| 2005/0129172 A1 | 6/2005 | Mertelmeier |

FOREIGN PATENT DOCUMENTS

| | | |
|---|---|---|
| DE | 0 368 067 | 5/1990 |
| WO | WO 00/57788 | 10/2000 |
| WO | WO 01/60236 A2 | 8/2001 |

OTHER PUBLICATIONS

Smith; Full Field Breast Tomosynthesis; website: www.directray.com/wh/pdf/W-LM-TOMO_Tomosynthesis.pdf; 6 pages.

* cited by examiner

*Figure 1*

(Prior Art)

TOMOGRAPHY SYSTEM

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates generally to tomography and to tomosynthesis systems and more particularly to a tomography system that provides improved three-dimensional breast imaging of tissue.

BACKGROUND OF THE INVENTION

As is known in the art, two techniques for acquiring images of body sections are tomosynthesis and tomography.

In tomosynthesis, a plurality of images are acquired as a radiation source traverses a path relative to the object being imaged. The radiation source emits a radiation signal (typically collimated) which impinges upon the object being imaged. At least portions of the emitted radiation signal propagate through the object and are sensed or detected by a fixed detector located on an opposite side of the object from the source.

The images acquired by the detector are combined (reconstructed) by a system of back-projection, error calculation and correction, and forward projection repeated one or more iterations until a stopping criteria (including one of iteration count) is reached. It is possible to reconstruct any plane in the object being imaged that is parallel to the detector. Generally, features of structures outside of the tomosynthesis plane of interest are of reduced intensity do not align precisely when they are so combined, which results in a depth-dependent reinforcement of in-plane, and diminution of out-of-plane structures. These out-of-plane structures are superimposed into the reconstructed plane, which can degrade the overall reconstructed image quality and results in an image having relatively low depth resolution.

While the above-described tomosynthesis technique has proven useful for detecting early forms of breast cancer, it is still possible for the detection of breast cancer to be missed by a physician or radiologist reviewing the data. For example, breast cancer may be missed by being obscured by radiographically dense, fibroglandular breast tissue or positioned inadequately outside the imaging volume for example.

The tomosynthesis technique of imaging tissue also generally requires that the detector and the object being imaged (e.g. a breast) be maintained in a stationary or fixed position while the radiation source is moved and positioned for obtaining the plurality of images. This limits the range over which the source can be moved and thus limits the number of different angles of images available to provide the final reconstructed image of the object Similar to tomosynthesis systems described above, tomography systems also incorporate a radiation source and a detector. In contrast to tomosynthesis systems, tomography systems move both the radiation source and the detector mutually about the object being imaged.

In a tomography system, a plurality of images are acquired as a collimated radiation source traverses a path relative to the object being imaged. The radiation source emits a radiation signal which impinges upon the object being imaged. At least portions of the emitted radiation signal propagate through the object and are sensed or by a detector or detectors located on an opposite side of the object from the source. As mentioned above, in a tomography system, both the radiation source and the detector traverse a path about the object being imaged while the object itself is maintained in a stationary position. In one prior art scheme, the source and detector are translated back and forth and at the end of each translation the source and detector are incremented rotationally to maintain a fixed spatial relationship. Signals corresponding to detected density variations are fed into a computer which, when information from the whole scan is complete, produces data representative of density variations in a plane which is transverse to the translation direction through which the source and detector are moved. An image can then be constructed from the data.

One drawback associated with such tomography systems when applied to certain imaging problems such as breast imaging is that the most desirable source and/or detector path can physically intersect with the body or organ being imaged (e.g. a breast). This is due, in part, because the location of the point or axis about which the radiation source and detector move is typically located proximate the object being imaged. Another drawback associated with tomography systems is that to compensate for the limited movement of the system about a path surrounding the object being imaged, the source provides a larger area of radiation which can result in radiating structures that are not of interest. For example, when it is desired to perform breast imaging, it may be necessary to also expose the chest, shoulder and heart/lungs of the person to radiation in order to provide sufficient data to accomplish the breast tomography.

It would, therefore, be desirable to provide a tomography system that allows imaging of an entire object without having source, detector or support structures intersect with the object or body of the subject being imaged. It would also be desirable to provide a system which reduces the amount of radiation directed toward structures not being imaged. It would be further desirable to provide a breast imaging system in which a source and detector are able to move over a relatively wide range of angles to allow a clinically useful set of measurements to be made.

SUMMARY OF THE INVENTION

In accordance with the present invention, a measurement system is presented. The measurement system includes a movable radiation source, a movable radiation detector located a set distance from the source with the source and detector both being moveable about a point, an axis or a plane located proximate the detector. The source and detector move in unison to maintain a desired spatial relationship which allows collection of tomographic data. The object being imaged is maintained in a fixed position while the source and the detector are movable about the point located proximate the detector. In one embodiment, the point is located at or below the detector to permit movement of the detector and any detector support structure without intersecting with any portion of an object being measure and without intersecting with any portion of any structure associated with the object being measured. In another embodiment, the point is located in a plane which is coincident with a plane defined by a first surface of the detector. In still another embodiment, the point is located on an edge of the detector. In still another embodiment, the point is provided as a pivot axis disposed proximate an upper or lower surface of the detector. In yet another embodiment, the point is provided as pivot point disposed proximate an edge or a surface of the detector. In short, the point can be provided at any location proximate the detector which allows the detector and any associated detector support structure to move without intersecting with the object being measured or any structure associated with the object being measured. The source and detector can move along a circular-shaped path, an elliptically-shaped path or a random polygonal-shaped path. Depending upon the particular path shape along which the source and detector move, a particular location proximate the detector about which movement of the source and detector occurs can be selected. The point about which movement of the source and detector occurs can be provided as a pivot point, an axis or a plane. In one embodiment, the point is provided as an axis of rotation proximate the detector and the source and detector are coupled together via a support arm which moves (rotates) the source and detector in unison about the axis of rotation.

By spacing the radiation source a set distance from the detector and allowing both the detector and the source to move about a point located proximate the detector, the measurement system can provide imaging measurements of an entire object without intersecting with the any part of the object being imaged or other structures associated with the object being imaged. Thus, the source and detector can traverse a relatively wide range of angles. Since the source and detector can traverse a relatively wide range of angles, a source which emits a radiation beam having a relatively narrow beamwidth and/or beamshape can be used. By using a source which emits a radiation signal having a relatively narrow beamwidth and/or beamshape, a system which reduces the amount of radiation directed toward structures not being imaged is provided.

In a breast imaging system, utilization of a separated source and detector which are movable about a point located proximate the detector in a synchronized and tailored source-detector motion results in a system in which the source and detector can move without intersecting or interfering with a person's body. Thus, the source and detector can traverse a range of angles which is wider than a range of angles achievable with prior art systems. By moving the point about which the source and detector move to a location proximate the detector, it is possible to move the detector high into the axilla region of a person's body and also to cover upper abdominal regions of the person's body. This results in the system being able to provide an improved medial lateral oblique projection (MLO projection).

Since the source and detector can be moved to positions not possible to reach with prior art systems, the system can measure data which can not be measured with prior art systems. This can result in a more clinically useful set of measurements. By measuring additional data not measurable by prior art systems, a breast imaging system which incorporates the features described hereinabove is able to provide more detailed and complete imaging than prior art breast imaging systems.

Furthermore, since the source has a wider range of travel, the system can utilize a source which provides a radiation beam having a cone shape and a beamshape selected to lessen the amount of radiation impinging upon structures that are not of interest. For example, in breast imaging applications, it is possible to lessen the amount of radiation which impinges upon a person's chest, shoulder, heart and lungs.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
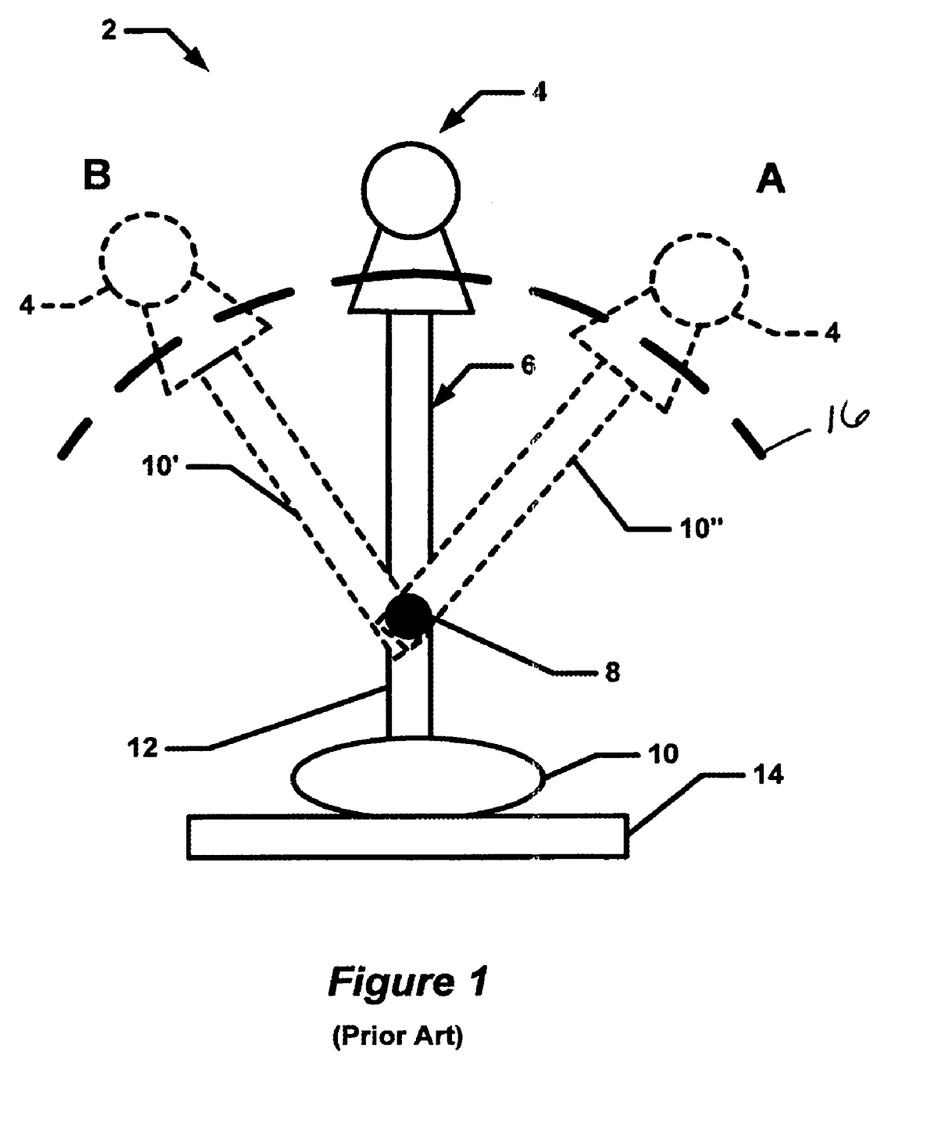
FIG. 1 is a block diagram of a prior art system for breast tomosynthesis.

Referring now to FIG. 1, a prior art tomosynthesis system 2 is shown. This system is similar to one described in U.S. Pat. No. 5,872,828 to Niklason et al. and assigned to the assignee of the present application. The system 2 includes a radiation source 4 attached to a movable arm 6. Movable arm 6 pivots about an axis or pivot point 8, located between the source 2 and an object 10 being imaged (e.g. a breast). A fixed arm 12 has a first end attached to a radiation detector 14 and a second end attached to the movable arm 6 at the pivot point 8. The object being imaged 10 (e.g., a human breast) is disposed abutting the detector 14. Typically the object 10 being imaged is compressed against the detector 14.

In use, the source 4 is rotated between the source position denoted A and the source position denoted B. The source 4 provides radiation to the detector 14 while moving along the arc 16 between the two positions A, B shown in FIG. 1. The detector 14 remains stationary. From the information collected by detector 14, a final synthesized representation of the X-ray absorption of the object 10 is produced as is generally known.

Figure 2:
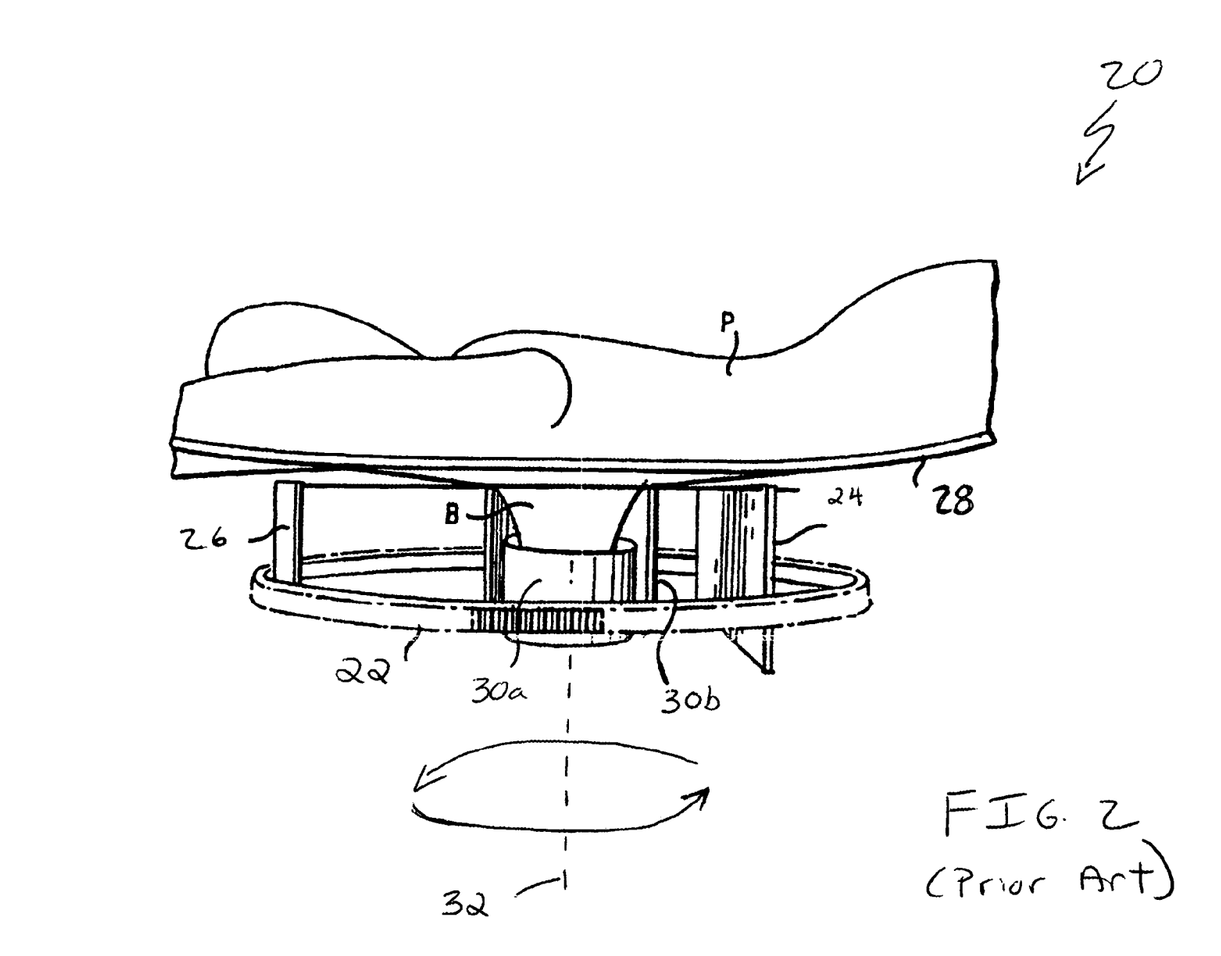
FIG. 2 is a block diagram of a prior art system for breast tomography.

Referring now to FIG. 2, a system for performing cone beam volume CT breast imaging 20 includes a gantry frame 22 on which a cone-beam radiation source 24 and a digital area detector 26 are mounted. A patient P rests on an ergonomically designed table 28 having a hole (or two holes) provided therein to allow one breast B (or two breasts) to extend through the table 28 into a breast holder having an inner portion 30a and an outer portion 30b. In this configuration the gantry frame 22 surrounds the breast B. Thus, the entire breast B can be exposed to the cone beam provided by the source 24.

The gantry frame 22 is rotatable around an axis 32 which is substantially centered in the breast B. Thus, the radiation source 24 and the detector 26 move about axis 32 in unison in a circular orbit around the breast while the breast remains in the path of the cone-shape radiation beam emitted by the source 24. The system shown in FIG. 2 is similar to the type described in U.S. Pat. No. 6,480,565 to Ning and assigned to the University of Rochester.

Figure 3:
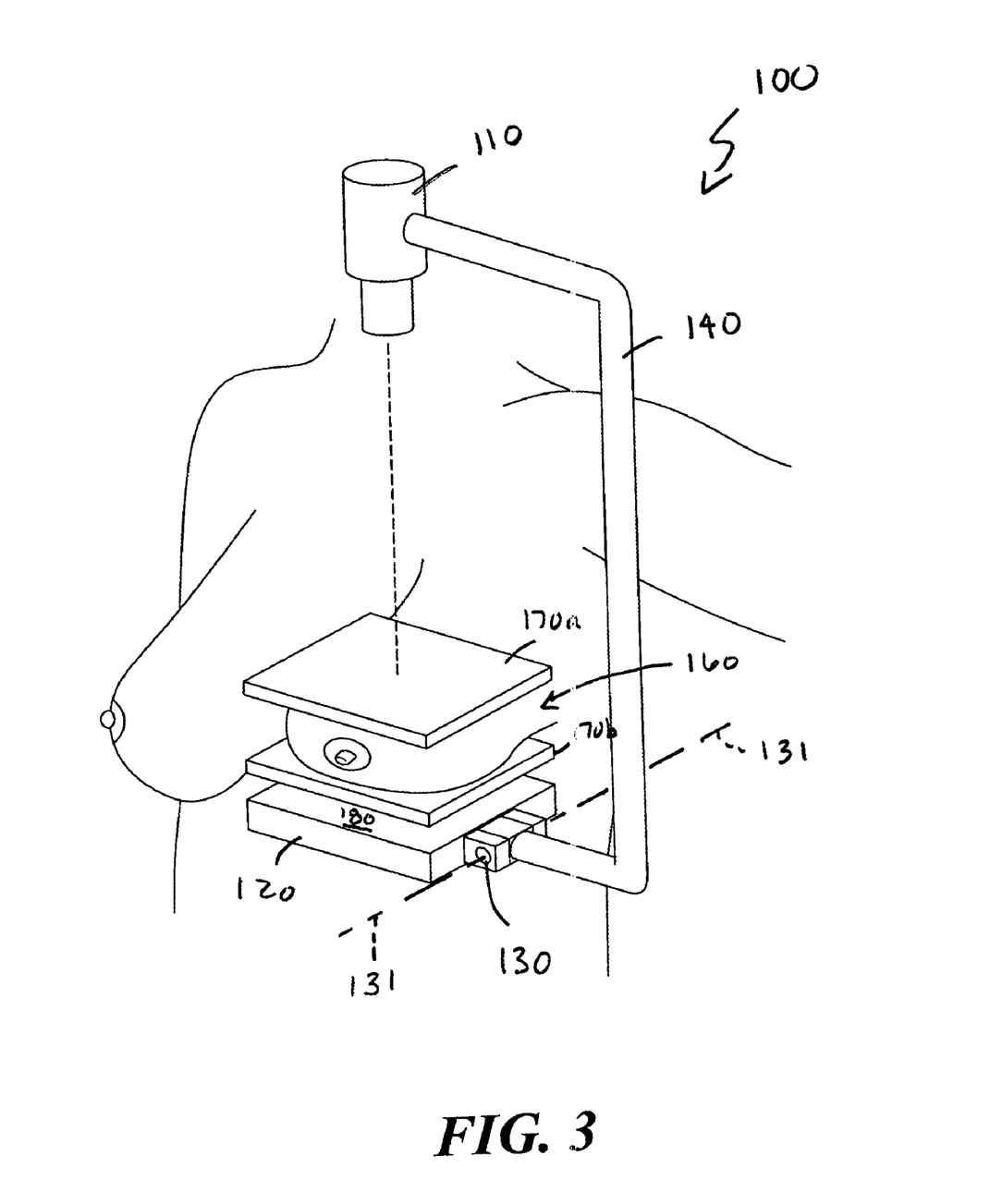
FIGS. 3 and 3A is a block diagram of a first embodiment of a limited angle conebeam breast tomography system.
Figure 3A:
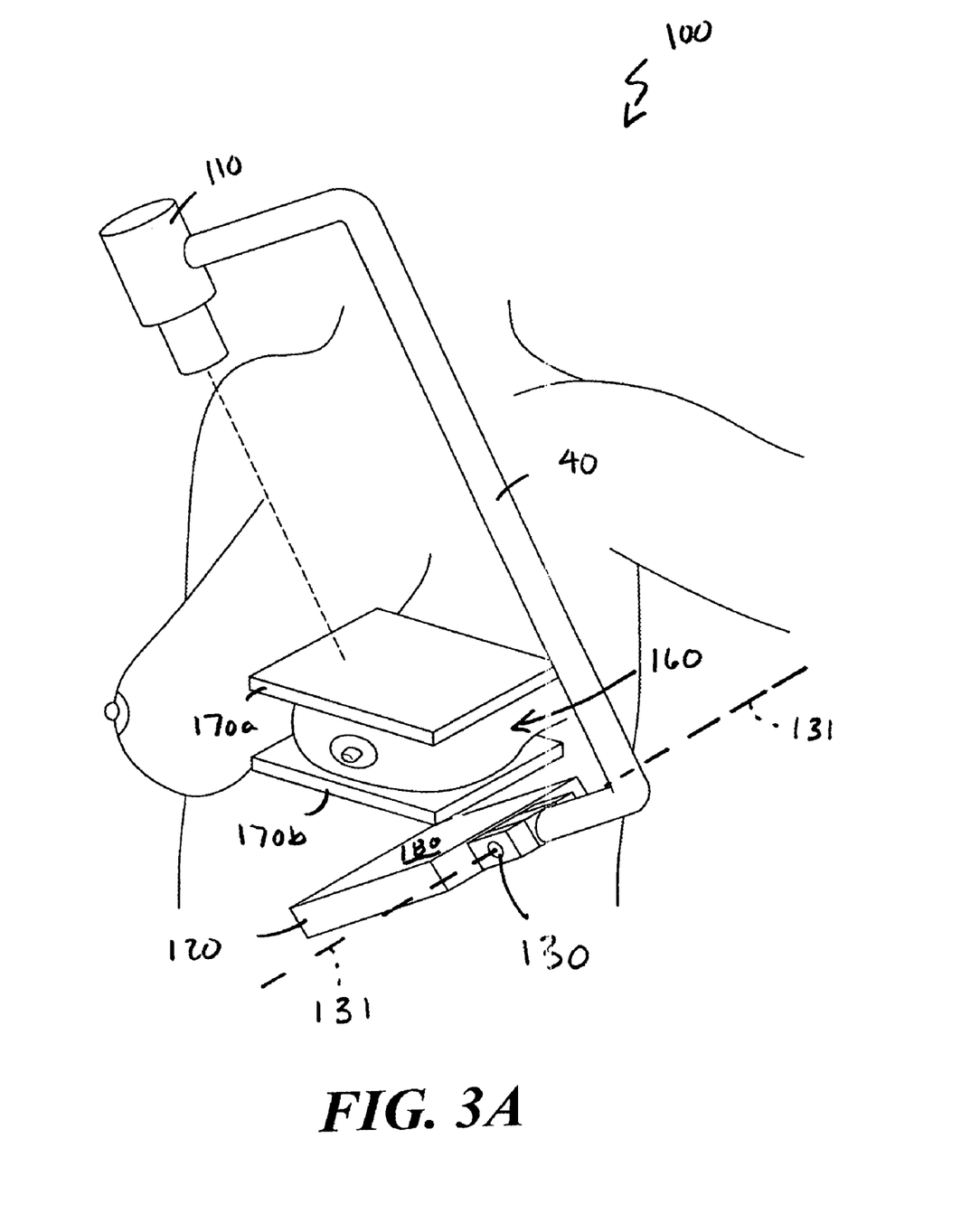

Referring now to FIGS. 3 and 3A in which like elements are provided having like reference designations, a breast tomography system 100 includes a source 110 (e.g. an x-ray source) and a detector 120. Surfaces of the source and detector are spaced from each other by a distance which does not change during operation of the tomography system 100. The detector is here shown as a digital planar detector although other detectors known to those of ordinary skill in the art and having either flat or curved surface, may of course also be used. It should be appreciated that only the source, detector and mounting arms are shown in FIGS. 3 and 3A and that for clarity and ease of description, other parts of the breast tomography system are not shown in FIGS. 3 and 3A.

In the exemplary embodiment of FIG. 3, the source 110 and detector 120 are coupled to first and second opposing ends of a support arm 140. An object to be imaged (e.g. breast 160) is disposed in a support 170 which is decoupled from the source 110, detector 120 and arm 140, such that the support 170 (and therefore the object 160 held in support 170) do not move during movement of the source 110, detector 120 and arm 140. A grid 180 coupled to a top surface of the detector 120 rejects scatter which can occur when the source 110 provides a radiation signal.

The arm 140 (and thus the source and detector coupled to the arm 140) moves about a point 130 located proximate the detector 120. In the exemplary embodiment of FIGS. 3 and 3A, point 130 lies in a plane in which the detector 120 lies. As the arm 140 moves, the source 110, detector 120 and arm 140 move through a path (e.g. an arc-shaped path) to the positions shown in FIG. 3A. Throughout the movement between positions, the detector 120 maintains a spatial relationship with the source 110 consistent with breast tomography techniques.

In operation of the tomography system 100, the radiation source 110 emits a beam of radiation toward the detector 120 and the source and detector pivot about the point 130. Throughout this motion, the breast 160 and the detector 120 are disposed in the path of the radiation emitted by the source 110 and the source 110 and detector 120 maintain a known spatial relationship in accordance with conventional breast tomography techniques. The detector 120 detects the presence of any radiation which passes through the breast 160 and reaches the detector 120.

In the case where the system 100 is used to perform breast tomography, a person is positioned as shown in FIGS. 3 and 3A and the breast being imaged (i.e. breast 160 in FIGS. 3 and 3A) is placed and compressed between compression plates 170a, 170b. It should be appreciated that the breast may be supported or held in some other manner rather than via the compression plates 170a, 170b. Regardless of how the breast is supported or held, the source 110 and detector 120 move to measure data over a range of angles which is wider than possible with prior art breast imaging techniques utilized with a person in the standing position. The data will later be used to provide images of the breast.

Since the point 130 about which the source 110 and detector 120 moves is physically located proximate the detector 120 and/or in a plane of the detector 120, neither the source 110, nor the detector 120, nor the arm 140 interfere with or intersect with the body during movement of the arm 140, the source 110 and the detector 120. Thus, it is possible to obtain images over a wide range of angles without requiring the person whose breast is being image to lie down.

This is in contrast to some prior art breast imaging systems in which if the torso of the person is adjacent a portion of a support arm, the detector and/or arm of the system will eventually interfere with a body part (i.e. the source and/or detector will physically intersect with a body part of the person) thus interfering with the motion of the system and thus limiting the range of angles over which the, detector and/or arm of the system can be moved.

Since in accordance with the present invention the source 110 and detector 120 can be moved to positions not possible with prior art systems, the system 100 can provide data which cannot be provided with prior art systems. Thus, the system 100 is able to provide more detailed imaging than prior art systems.

Furthermore, since the source 110 can traverse a range of angles which is wider than the range available in prior art systems, the source 110 can utilize a radiation beam having a cone shape which has a beamwidth and/or beamshape which is narrow compared with the beamwidth and/or beamshape of cone-shaped beams used in prior art systems. This allows use of a radiation beam which lessens the amount of radiation which impinges upon structures that are not of interest. In breast imaging, for example, it is possible to lessen the amount of radiation which impinges upon a person's chest, shoulder, heart and lungs and it is also possible to lessen the amount of radiation which "spills over" the detector 120.

Moreover, the fixed relationship of the source 110 to the detector 120 permits the use of grid 180 that provides grid-based scatter rejection and therefore a higher contrast resultant image.

A benefit which results from placing the point about which the source and detector move in or proximate a plane in which the detector 120 lies is that when the present system is used for breast tomography, the system allows increased measurements of the breast-to-chest area which is not possible with prior art tomography systems. This can result in the system being able to provide improved medial lateral oblique projections (MLO projections).

The above arrangement thus permits three-dimensional imaging of tissue such as a human breast, using a specific motion of the source 110 and detector 120 while holding the subject tissue (e.g. breast 160) immobilized.

It should be appreciated that alternate embodiments of the tomography system 100 of the present invention are also known. For example, although FIGS. 3 and 3A show the point about which the source and detector lies to be an axis in a plane of the detector, the point 130 may correspond to a pivot point, or a plane rather than an axis. Thus references made herein to a point about which the source and detector move are not limited to a specific point but rather are intended to include any point implemented as a pivot point, an axis, a plane or any other structures. Also the point may be located in other positions. In particular, the point about which the source and detector move may be located coincident with, above or below a plane in which a surface of the detector lies. The point about which the source and detector move may correspond to a pivot point or an axis or a plane which is horizontally displaced from the junction of the detector 120 and arm 140. In some embodiments it may be possible to locate the point slightly above a plane in which the detector lies. It should, however, be appreciated that in the case where the point is above a plane in which the detector lies, the point must be located proximate the detector such that no structure interferes or intersects with a person during operation of the system. That is to say, the point about which source 110 and detector 120 move should be selected such that the source and detector are able to pivot or otherwise move freely (e.g. rotate) without interfering with (e.g. physically contacting) a subject or patient. The location of all the pivot points/axis provide for a system that does not interfere with or intersect with the body during traversal of the source and detector during the process of generating tomographic breast images.

It should also be appreciated that in some embodiments the source and the detector may be independent of one another while still moving about the same point. Thus, rather than the source and detector being coupled together via a physical structure (e.g. by support arm 140 in FIGS. 3 and 3A) such that they must move in unison, the source 110 and detector 120 can be movable independently from another and their movements are coordinated such that they move in synchronization about the same point in order to maintain a fixed distance and spatial relationship between each other.

A measurement system has been described. The measurement system includes a movable radiation source, a movable radiation detector located a selected distance from the radiation source with the source and the detector movable about a point, an axis or a plane located proximate the detector. By providing a configuration wherein the source and the detector are movable about a point, an axis or plane proximate the detector, the system does not interfere with the subject or require irradiation of body structures that are not of interest and at the same time enables a set of measurements to be made which may be more clinically useful than measurements enabled by prior art systems.

Having described preferred embodiments of the invention it will now become apparent to those of ordinary skill in the art that other embodiments incorporating these concepts may be used. Accordingly, it is submitted that that the invention should not be limited to the described embodiments but rather should be limited only by the spirit and scope of the appended claims.

What is claimed is:

1. A measurement system comprising:
   a detector having first and second opposing surfaces and an edge surface, said detector rotatable about a pivot point located proximate an edge of said detector and in a plane in which the detector lies; and
   a source disposed a predetermined distance from said detector and arranged to emit a signal toward said detector with the source movable about the same pivot point as the detector and with the source and detector adapted to maintain a spatial relationship which allows collection of tomographic data.

2. The system of claim 1 further comprising a support arm coupled to said source and said detector in wherein said arm is movable about the pivot point.

3. The system of claim 1 wherein said source and said detector are coupled such that movement of said source results in a corresponding movement of said detector.

4. The system of claim 1 further comprising a support element disposed to hold an object to be imaged in a fixed position.

5. The system of claim 4 wherein said support element comprises:
   a first plate; and
   a second plate spaced a predetermined distance from and generally parallel to said first plate, and wherein the object to be imaged is supported between said first plate and said second plate.

6. The system of claim 1 wherein said detector and said source are coupled via a control system such that movement of a first one of said source and said detector results in a corresponding movement of a second one of said source and said detector to maintain the source and detection in a spatial relationship which allows collection of tomographic data.

7. A breast tomography system comprising:
   a detector having first and second opposing surfaces and an edge surface, said detector rotatable about a pivot point located proximate an edge of said detector and in a plane in which the detector lies;
   a source disposed a predetermined distance from said detector and arrange to emit a signal toward said detector with the source movable about the same pivot point as the detector and with the source and detector adapted to maintain a spatial relationship which allows collection of tomographic data.
   a support arm having a first end coupled between said source and said detector wherein said support arm has an axis of rotation at the pivot point and wherein each of said source and detector move rotationally about the pivot point in response to movement of said support arm.

8. The system of claim 7 wherein movement of said source and movement of said detector are synchronized to maintain approximately a same distance between said source and said detector.

9. The system of claim 7 further comprising a support element disposed between said source and said detector, said support element comprising:
   a first plate; and
   a second plate spaced a predetermined distance from and generally parallel to said first plate, with the first and second plates adapted to support a breast.

10. The system of claim 7 wherein said support arm has a first end coupled to said source and a second opposite end coupled to said detector.

11. The system of claim 10 wherein said support arm has a generally U-shape.

12. The system of claim 11 wherein said source comprises an X-ray source.

13. The system of claim 12 wherein said detector comprises an X-ray detector.

14. A breast tomography system comprising:
   a detector having first and second opposing surfaces and an edge surface, said detector rotatable about a pivot point located proximate an edge of said detector and in a plane in which the detector lies;
   a source disposed a predetermined distance from said detector and arranged to emit a signal toward said detector, said source movable along an arc having a radius measured from the same pivot point as said detector such that said source moves about the pivot point and wherein in response to movement of said source and said detector, said source and said detector are adapted to maintain a spatial relationship which allows collection of tomographic data.

15. The system of claim 14 wherein the pivot point corresponds to an axis about which the source and detector move and wherein the location of the axis is selected from the group consisting of:
   a location substantially coincident with a plane defined by the first surface of said detector;
   a location substantially coincident with a plane defined by the second surface of said detector; and
   a location which is in a plane which is located between a plane defined by the first surface of said detector and a plane defined by the second surface of said detector.

16. The system of claim 15 wherein movement of said source and movement of said detector are synchronized to maintain a fixed distance between said source and said detector.

17. The system of claim 14 wherein said source is movable along an arc having a radius measured from the pivot point about which said detector rotates.

18. The system of claim 14 further comprising a support arm having a first end coupled to said source and a second end coupled to said detector, said support element having a shape selected to maintain a spatial relationship which allows collection of tomographic data.

19. The system of claim 14 wherein said support arm is provided having a generally U-shape.

* * * * *

UNITED STATES PATENT AND TRADEMARK OFFICE
CERTIFICATE OF CORRECTION

PATENT NO. : 7,298,816 B2  Page 1 of 1
APPLICATION NO. : 11/195463
DATED : November 20, 2007
INVENTOR(S) : Moore et al.

It is certified that error appears in the above-identified patent and that said Letters Patent is hereby corrected as shown below:

Column 2, line 6 delete "sensed or by a" and replace with --sensed by a--.

Column 2, line 63 delete "measure" and replace with --measured--.

Column 3, line 28 delete "intersecting with the any" and replace with --intersecting any--.

Column 3, line 55 delete "can not" and replace with --cannot--.

Column 4, line 49 delete "configuration the" and replace with --configuration, the--.

Column 5, line 55 delete "image" and replace with --imaged--.

Column 5, line 65 delete "invention the" and replace with --invention, the--.

Column 6, line 47 delete "embodiments it" and replace with --embodiments, it--.

Column 7, lines 15-16 delete "invention it" and replace with --invention, it--.

Column 7, line 63 delete "arrange" and replace with --arranged--.

Column 7, line 67 delete "data." and replace with --data;--.

Signed and Sealed this

Fifteenth Day of April, 2008

JON W. DUDAS
*Director of the United States Patent and Trademark Office*